(12) United States Patent
King et al.

(10) Patent No.: US 8,957,256 B2
(45) Date of Patent: Feb. 17, 2015

(54) PROCESS FOR MAKING ETHERS FROM ALKOXIDE ANIONS OR PRECURSORS OF ALKOXIDE ANIONS

(75) Inventors: Stephen W. King, League City, TX (US); Richard R. Mitford, Langley Park (GB); Jeffrey G. Hippler, South Charleston, WV (US)

(73) Assignee: Dow Global Technologies LLC, Midland, MI (US)

( * ) Notice: Subject to any disclaimer, the term of this patent is extended or adjusted under 35 U.S.C. 154(b) by 791 days.

(21) Appl. No.: 12/680,022

(22) PCT Filed: Sep. 22, 2008

(86) PCT No.: PCT/US2008/010967
§ 371 (c)(1),
(2), (4) Date: Jul. 16, 2010

(87) PCT Pub. No.: WO2009/042091
PCT Pub. Date: Apr. 2, 2009

(65) Prior Publication Data
US 2010/0280277 A1 Nov. 4, 2010

Related U.S. Application Data

(60) Provisional application No. 60/995,574, filed on Sep. 26, 2007.

(51) Int. Cl.
*C07C 41/16* (2006.01)
*C07C 43/11* (2006.01)

(52) U.S. Cl.
CPC ..................................... *C07C 41/16* (2013.01)
USPC .......................................... 568/618; 568/613

(58) Field of Classification Search
USPC ................................................. 568/618, 615
See application file for complete search history.

(56) References Cited

U.S. PATENT DOCUMENTS

| | | | |
|---|---|---|---|
| 2,588,771 A * | 3/1952 | Schwartz | 568/45 |
| 2,649,166 A | 8/1953 | Porter et al. | |
| 2,924,621 A * | 2/1960 | Krey et al. | 568/660 |
| 3,362,133 A | 1/1968 | Kutsher et al. | |
| 3,591,641 A | 7/1971 | Ameen et al. | |
| 3,634,522 A * | 1/1972 | Smith et al. | 568/673 |
| 3,737,392 A | 6/1973 | Ameen et al. | |
| 3,824,766 A | 7/1974 | Valentine et al. | |
| 3,837,143 A | 9/1974 | Sutherland et al. | |
| 3,959,391 A * | 5/1976 | Allain | 568/619 |
| 4,044,100 A | 8/1977 | McElroy, Jr. | |
| 4,435,586 A * | 3/1984 | Kruse et al. | 549/464 |
| 4,581,154 A | 4/1986 | Kutsher et al. | |
| 4,741,745 A | 5/1988 | Kadono et al. | |
| 4,946,620 A | 8/1990 | Kadono et al. | |
| 4,995,888 A | 2/1991 | Beaupre et al. | |
| 5,273,679 A | 12/1993 | Hihara et al. | |
| 6,592,779 B1 | 7/2003 | Burns et al. | |
| 2008/0132648 A1 * | 6/2008 | Snell et al. | 525/328.8 |

FOREIGN PATENT DOCUMENTS

| | | | | |
|---|---|---|---|---|
| EP | 0021497 | | 1/1981 | |
| EP | 0146886 | | 7/1985 | |
| EP | 0770420 | | 5/1997 | |
| WO | WO03046048 | * | 6/2003 | C07C 41/16 |

OTHER PUBLICATIONS

Smith, R.G. et al., "Dimethyl sulfoxide as a solvent in the Williamson ether synthesis," Canadian Journal of Chemistry, vol. 47, pp. 2015-2019, 1969.

* cited by examiner

*Primary Examiner* — Rosalynd Keys
(74) *Attorney, Agent, or Firm* — Kagan Binder, PLLC

(57) ABSTRACT

Improved methods for making ethers. In particular, an alkoxide can be more effectively converted into an ether by reaction with a hydrocarbyl halide in the presence of a substantial excess of a hygroscopic base such as NaOH. When present in such an unconventional excess, the base serves multiple functions. As a consequence, the alkoxide is extensively converted to the desired ether rapidly at excellent yields. The reaction environment also aids later product isolation. The use of the NaOH rather than Na metal allows the ether product to be separated from water soluble impurities such as salt products, left over base, left over hydrocarbyl halide, formates, etc. by liquid-liquid extraction among aqueous and organic phases.

13 Claims, No Drawings

PROCESS FOR MAKING ETHERS FROM ALKOXIDE ANIONS OR PRECURSORS OF ALKOXIDE ANIONS

CROSS-REFERENCE TO RELATED APPLICATIONS

This application claims benefit from International Application No. PCT/US2008/010967, filed Sep. 22, 2008, having International Publication No. WO 2009/042091, which in turn claims priority to U.S. Provisional Application Ser. No. 60/995,574, filed Sep. 26, 2007, entitled "PROCESS FOR MAKING ETHERS FROM ALKOXIDE ANIONS OR PRECURSORS OF ALKOXIDE ANIONS" which applications are incorporated herein by reference in their entireties for all purposes.

FIELD OF THE INVENTION

The present invention relates to methods of making ethers by reacting a metal alkoxide with a hydrocarbyl halide. In particular, the metal alkoxide is converted into an ether by reacting with a hydrocarbyl halide in the presence of a base such as sodium hydroxide.

BACKGROUND OF THE INVENTION

Ethers are commercially important compounds, and a wide variety are known. Many are used with respect to solvents, propellants, fillers, food additives, fuel additives, cleaners, health care formulations, manufacture of polymers, etc. Ethers include polyether oligomers and polymers such as the polyoxyalkylene oligomers and polymers. Polyethyleneglycols, based upon repeating units of oxyethylene, are a type of polyoxyalkylene oligomer and are very widely known and used. These incorporate multiple ether linkages along the body of the molecule. These may also have one or more terminal ether groups. Polyoxyalkylene products often are commercially available as a mixture containing a distribution of oligomers and/or polymers with varying number of repeating units and a corresponding variation in molecular weight.

Linear polyoxyalkylene materials with terminal ether groups at each end are commonly used as solvents in the chemical industry. These solvents are also referred to as polyalkylene glycol dialkyl ethers and are well known as solvents for acidic gases such as carbon dioxide, hydrogen sulfide, carbonyl sulfide, carbon disulfide, mercaptans, and the like. These solvents are used to scrub such acid gases from process streams. These solvents are described in U.S. Pat. Nos. 2,649,166; 3,362,133; 3,591,641; 3,737,392; 3,824,766; 3,837,143; 4,044,100; 4,581,154; 4,741,745; 4,946,620; 4,995,888; 5,273,679; and 6,592,779. See also EP 146886. It is well known from these patent documents that the dialkyl ethers of polyoxyalkylene glycols, and in particular the dimethyl ethers, comprise mixtures of polyoxyalkylene adducts typically ranging from 1 to 9 units of the oxyethylene moiety.

The Williamson ether synthesis was developed by Alexander Williamson in 1850. This synthesis involves converting an alkoxide ion to an ether by reaction with a hydrocarbyl halide. The Williamson synthesis continues to be widely used, and indeed, is applied to the synthesis of polyoxyalkylene materials with terminal ether groups. In the manufacture of such materials, a linear polyoxyalkylene having an ether group at one end and an alcohol at the other end serves as an alkoxide precursor. In the presence of Na or a strong base, the alcohol is converted to the corresponding alkoxide. This alkoxide reacts with a hydrocarbyl halide to form the desired diether.

The synthesis of polyalkyleneglycol dimethyl ethers has been described in EP 146886 and U.S. Pat. No. 3,591,641. These patents use Na metal as a reactant to form alkoxide anion and then filter or centrifuge to remove the sodium chloride byproduct. The use of sodium metal requires extreme care in its use and necessitates venting of hydrogen gas from the reactor. Relying upon filtering or centrifuging to remove sodium chloride also results in a substantial loss of product. The captured sodium chloride also has to be cleaned before it can be discarded or recycled.

An alternative process for making polyalkyleneglycol dimethyl ethers has used NaOH as the reactant to form alkoxide. However, unlike the present invention, this early process only used a modest stoichiometric molar excess of the base relative to the alkoxide on the order of about 0.1 to 0.2 equivalent stoichiometric excess. This process suffers from yield issues. The dimethyl ether products may also suffer from color issues causing them to fail to meet color specifications consistently. For instance, color specifications might specify that the dimethyl ether product has a Gardner number of less than 3, which might serve as a qualitative measure of product purity, corresponding to a relatively clear, relatively colorless product. Yet, some product according to this process might have a Gardner number on the order of about 10, which suggests a substantial amount of impurities in the product that could affect the ability of the material in its intended end use application.

Improved methods for making ethers, particularly diethers, more particularly diethers of polyoxyalkylene materials, are highly desired.

SUMMARY OF THE INVENTION

The present invention provides improved methods for making ethers. In particular, an alkoxide can be more effectively converted into an ether by reaction with a hydrocarbyl halide in the presence of a substantial stoichiometric excess of a hygroscopic base such as NaOH. When present in such an unconventional excess, the base serves multiple functions. As a consequence, the alkoxide is extensively converted to the desired ether rapidly at excellent yields. The reaction environment also aids later product isolation. The use of NaOH rather than Na metal allows the ether product to be formed at higher efficiencies and can be easily removed with other water soluble impurities such as salt products, left over base, hydrocarbyl halide, etc. by liquid-liquid extraction among aqueous and organic phases.

The use of a substantial excess of a hygroscopic base allows a larger amount of the metal alkoxide to be formed from the alcohol without concurrent removal of water overhead. As a result, the reaction can proceed to greater than 98 percent completion to the desired ether with minimum byproducts being formed (lower alcohols and ethers of lower alcohols).

The present invention also offers strategies to minimize color issues to help ensure that ethers prepared from monoalkylether polyoxyalkylene alcohols can meet applicable color specifications (e.g., Gardner specifications) where applicable. The present invention also offers strategies to minimize the production of formate by-products.

The process techniques of the invention can be applied to the manufacture of a wide range of ethers. These include monoethers, but the invention is particularly useful for making diethers. For example, the invention can be used to readily convert monoalkylpolyoxyalkylene alcohols to their dialkyl ether counterparts via reaction with a suitable hydrocarbyl halide.

The process techniques of the invention can be carried out at a wide range of temperatures, including temperatures above and below 110° C. Uniquely, by using an atypically high concentration of hygroscopic base and efficient agitation, the reaction can be carried out at surprisingly low temperatures as well.

In one aspect, the present invention relates to a method of making an ether, comprising the steps of:
a) reacting an alcohol with at least a 20 molar percent stoichiometric excess of a water-soluble hygroscopic base to form an intermediate product mixture comprising an alkoxide anion, remaining alcohol, excess base; and
b) in the presence of the excess base and the remaining alcohol, adding a hydrocarbyl halide to the intermediate product mixture and reacting the alkoxide anion with the hydrocarbyl halide to form a product mixture comprising an ether.

In another aspect, the present invention relates to a method of making an ether, comprising the steps of:
a) reacting an alcohol with at least a 20 molar percent stoichiometric excess of a water-soluble hygroscopic base to form an intermediate product mixture comprising an alkoxide anion, excess base; and
b) adding a hydrocarbyl halide to the intermediate product mixture and reacting the alkoxide anion with the hydrocarbyl halide to form a product mixture comprising an ether, wherein at least a portion of the excess base is in the form of suspended particles during at least a portion of the reaction between the hydrocarbyl halide and the alkoxide anion.

In another aspect, the present invention relates to a method of forming an ether, comprising the steps of:
a) providing a reaction medium comprising suspended particles of a hygroscopic base and an alcohol reactive with the base to form an alkoxide; and
b) reacting the alkoxide with a hydrocarbyl halide in said reaction medium, said reaction occurring in said reaction medium at a temperature at which at least a portion of said particles remain solid during at least a portion of the reaction.

In another aspect, the present invention relates to a method of making an ether, comprising the steps of:
a) reacting an alcohol with at least a 20 molar percent stoichiometric excess of a water-soluble hygroscopic base to form an intermediate product mixture comprising an alkoxide anion, remaining alcohol, excess base, said reacting occurring at a first temperature;
b) heating the intermediate product mixture to a second temperature greater than the first temperature;
c) optionally holding the intermediate product mixture at a third temperature greater than the first temperature; and
d) in the presence of the excess base and the remaining alcohol, adding a hydrocarbyl halide to the intermediate product mixture and reacting the alkoxide anion with the hydrocarbyl halide at a fourth temperature to form a product mixture comprising an ether.

DETAILED DESCRIPTION

In the practice of the present invention, wide ranges of ethers are formed by a methodology comprising two steps. In a first step, an alcohol is reacted with a substantial, stoichiometric excess of a water soluble, hygroscopic base to form an alkoxide anion. The first reaction step may be schematically represented as follows using NaOH as an illustrative hygroscopic, water-soluble base:

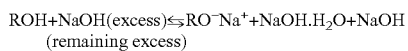
(remaining excess)

In a second reaction step, the alkoxide anion is reacted with a source of an alkyl moiety such as a hydrocarbyl halide or the like to form an ether. The second reaction step may be schematically represented as follows using an alkyl source R'X as an illustrative co-reactant:

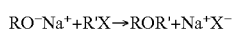

In these reaction steps, X represents one or more anion leaving groups, such as halide, tosylate, mesylate, combinations of these, and the like. For purposes of convenience, the reactant R'X will be referred to as a hydrocarbyl halide, even though it is understood that X encompasses leaving groups including but not limited to halide. In many embodiments, Cl⁻ is suitable as the anion leaving group. Each of R and R' independently is any straight, linear, or branched monovalent moiety other than H. In other words, apart from one or more other substituents or other moieties that might be incorporated into R, at least one valent site is allocated to a hydroxyl. In many embodiments, R may be alkyl, aryl, aralkyl, or the like; and RO can be (poly)oxyalkylene of the formula $R^1O-(R^2O)_n-$, wherein $R^1$ is a monovalent moiety other than H, often linear, straight, or branched alkyl of 1 to 20, desirably 1 to 5 carbon atoms, and n is 1 to 10,000 or is 1 to 10,000 on average when the (poly)oxyalkylene is a population of different species; and $R^2$ is alkylene of 1 to 5, desirably 1 to 3 carbon atoms. Specific examples of oxyalkylene units according to formula $-R^2O-$ Examples include $-CH_2O-$, $-CH_2CH_2O-$, $-CH_2CH_2CH_2O-$, $-CH_2CH(CH_3)O-$, $-CH(CH_3)CH_2O-$, $-CH_2CH(CH_3)CH_2O-$, other isomers of oxybutylene, combinations of these, and the like. The present invention is particularly useful for forming dialkylethers from monoether alcohol precursors, especially monoethers of (poly)oxyalkylene alcohols containing from 1 to 10,000, desirably 1 to 1,000, more desirably 2 to 15, oxyalkylene repeating units.

R desirably is a hydrocarbyl such as an aryl (such as benzyl), aralkyl, or an alkyl of 1 to 20 carbon atoms, desirably 1 to 10 carbon atoms, more desirably 1 to 3 carbon atoms, often methyl or ethyl. Preferably, R and R' are nonfunctional moieties. However, if either of R or R' includes functional groups, these may be masked in accordance with conventional masking strategies to protect them in the course of the ether reaction described herein. After the reaction between the alkoxide and the hydrocarbyl halide is completed, the functional groups can be unmasked.

In the first reaction step, the alcohol is converted to an alkoxide anion using a substantial stoichiometric excess of the base relative to the alcohol. Generally, if the excess of base is too low, then the reaction might proceed too slowly or the conversion to the desired product might be too low. If too much, the base could participate in side reactions, lowering yields, and/or cause corrosion of reaction vessels. Balancing such concerns, and as used herein, substantial stoichiometric excess means a stoichiometric excess of at least 20 molar percent, desirably at least 25 to 400 molar percent, more desirably at least 30 to 200 molar percent, even more desirably 35 to 150 molar percent, and most desirably 35 to 75 molar percent.

The base is preferably hygroscopic so that it serves both as base and a water scavenger (or desiccant). A separate water scavenger is not needed when a hygroscopic base is used.

This is highly desirable, inasmuch as this avoids having to separate the ether product from a separate water scavenger present as an additional ingredient. Of course, in some embodiments, a water scavenger could still be used in such embodiments if desired. As used herein, hygroscopic means that the base attracts, associates, with, and thereby removes as a practical matter, water molecules from the reaction medium via physical and/or chemical absorption, adsorption, or other desiccating mechanism. Thus, the hygroscopic base advantageously performs multiple functions. Firstly, the base functions as a reactant as it reacts with the alkoxide precursor, i.e., an alcohol, to form an alkoxide anion in situ. The base also scavenges water formed by the conversion of the alkoxide precursor to the alkoxide anion. This scavenging, in turn, helps to drive the reaction to completion. The use of a base such as NaOH also allows an easy liquid/liquid extraction to separate the ether product from salt and other water soluble by-products. In short, the base functions as reactant, desiccant, equilibrium driver, and isolation facilitator.

In addition to sodium hydroxide, an example of another hygroscopic base that could be suitable in the practice of the present invention might include KOH and the like. Sodium hydroxide is preferred and desirably is added as pellets, granules, or a powder to the reaction vessel.

In many modes of practice, the alcohol reactant and the ether product function as solvents for the process. Consequently, additional solvent may not be needed. It is possible, though, that some reaction mixtures may become relatively thick and hence be difficult to agitate. In such instances, using one or more inert, non-aqueous solvents such as acetonitrile or N,N-dimethylformamide may be desirable. In some instances, using a nonpolar, desiccating solvent such as cyclohexane may be desirable.

The first reaction step may be carried out in a typical embodiment by first charging the alcohol to a reaction vessel. The base can then be added. The vessel can be cooled to maintain the temperature below, for instance, about 40° C., during base addition. The addition of the base can occur slowly over a period of time, for instance from about 3 seconds to about 72 hours, more typically 0.5 to about 4 hours. The mixture is agitated well during the addition and throughout the course of the conversion to the alkoxide. After the addition of the base is complete, the mixture can be heated or chilled to the desired reaction temperature at which time the second reaction step will be carried out. As the reaction proceeds, the base scavenges the water product, helping to drive the formation of the alkoxide further to completion.

In the second reaction step, the reaction mixture desirably includes at least the stoichiometric amount and often a stoichiometric excess of the hydrocarbyl halide relative to the alkoxide anion. This helps ensure that as much of the alkoxide anion is converted as is practically feasible. The amount of excess, if any, will depend upon factors including the nature of the reactants, the reaction temperature (described further below), and the like.

The reaction between the alkoxide anion and the hydrocarbyl halide may occur at a wide range of temperatures such as from 35° C. to 150° C. A hydrocarbyl halide such as methyl chloride may have a greater tendency to participate in side reactions at higher reaction temperatures, e.g., those above about 110° C. While this might suggest that higher reaction temperatures should be avoided, using higher reaction temperatures may be desirable to minimize color issues (described further below), such as when forming diethers that are alkyl ether-capped (poly)oxyalkylenes or mixtures of these. To be able to access such higher reaction temperatures while minimizing color problems, relatively greater amounts of hydrocarbyl halide may be used to account for portions that might be consumed in side reactions. For instance, in one mode of practice, using at least about 1.1 equivalents of a hydrocarbyl halide per equivalent of a methoxyethylene glycol is suitable for a reaction carried out at 120° C.

On the other hand, when carrying out the reaction at lower temperatures, below about 110° C., desirably below about 50° C., side reactions are less of a concern. The hydrocarbyl halide is used much more efficiently. Under such circumstances, using a much more moderate excess or even no excess of the hydrocarbyl halide is suitable. For example, in one mode of practice, using the stoichiometric 1.0 equivalent of a hydrocarbyl halide per equivalent of a methoxyethylene glycol is suitable for a reaction carried out at 40° C. to 45° C.

In short, carrying out the process at lower temperatures helps to increase the efficient use of hydrocarbyl halide in many embodiments by reducing side reactions that tend to occur at higher temperatures. This advantageously helps to achieve the desired conversion in a shorter timescale. This also makes it possible to reduce the amount of hydrocarbyl halide to stoichiometric levels in some embodiments, in contrast to conventional processes that use the hydrocarbyl halide in substantial excess. Yet, use of lower temperatures may make it desirable to add agents to protect against coloration (described further below). Consequently, where coloration is at issue, higher temperatures are still desirably practiced to minimize coloration issues even though hydrocarbyl halide might not be used as efficiently.

The second reaction step is conveniently carried out directly in the same reactor as the first reaction step without any isolation or work up or removal of any of the contents of the reactor from the first step. This one pot reaction sequence is efficient and helps to improve overall conversion and yield. As noted above, the first reaction step is generally an equilibrium reaction. From the equilibrium perspective of the first reaction step, the second reaction step consumes a product (the alkoxide) of the first reaction step. This helps create an equilibrium driving force to convert more alcohol to alkoxide. In short, the occurrence of the second reaction step in the same pot helps more of the first reaction occur, leading to much higher conversion and yield. This means that as the second reaction step is occurring, additional first reaction is also occurring concurrently. Thus, it can be appreciated that the presence of excess base is beneficial during the second reaction step to provide reactant and desiccating functionality to allow the additional, concurrent first reaction to occur.

Conveniently, the hydrocarbyl halide may be added to the vessel through a dip tube that introduces the reactant at the vessel bottom. The addition may occur all at once or over an extended period of time. The reactants may be mixed and held at the reaction temperature for a suitable time period, such as 0.5 to 24 hours to allow the reaction to proceed.

The second reaction step desirably is carried out with sufficient agitation to facilitate good intermixing and homogeneity of the reactants during the course of the reaction. The reactants are thoroughly and vigorously mixed during the course of the reaction to facilitate conversion of the alkoxide to the desired ether. Such agitation is particularly important when using low reaction temperatures, e.g., temperatures less than 110° C., often less than about 75° C., and particularly less than about 50° C. At lower temperatures, the NaOH and the NaOH-water complexes will tend to be present as solids rather than melt/dissolve and be in the liquid phase. In this solid form, the NaOH and non-saturated complexes, particularly in finely divided form, are very effective desiccants, but must be adequately agitated to be kept in suspension. Advantageously, the finely divided, solid particles of NaOH and complexes thereof provide a large surface area for the formation of the alkoxide and for desiccant action. Without adequate agitation, this surface area might not be as readily available to the reactants. The corresponding reaction could be slower or otherwise compromised as a result. By comparison, the NaOH and complexes thereof can melt and enter the liquid phase at higher temperatures, where suspending finely divided solids is not an issue.

In one mode of practice, suitable NaOH particles in the so-called micropearl form as supplied by the supplier have a particle size distribution in the range from 100 microns to 1000 microns. After completion of the process, the particle size distribution was measured and found to be in the range from about 5 microns to 10 microns. This indicates attrition of the particles during the course of the process. Smaller particles, so long as they can be dispersed effectively, are preferred for their higher surface area.

A key advantage of the invention is the appreciation to carry out the second reaction step in the presence of the hygroscopic base in finely divided, solid form with agitation to maintain an even dispersion of the solids throughout the reaction medium during the second reaction step. These features surprisingly allow the second reaction step to be carried out using the stoichiometric amount of hydrocarbyl halide. Without this base being present, and without this base being well dispersed by such thorough agitation, the second step will not proceed adequately at such low temperatures.

After the second reaction step is complete, enough water can be added to the vessel to form two distinct liquid layers. One layer will be an aqueous layer containing salts and other water soluble species. The desired diether product will be in the organic layer and is easily separated from the aqueous layer. After separating the layers, the organic layer can be washed one or more additional times with water containing salt to upgrade the purity of the organic phase. Similarly, the aqueous layers can be back extracted to recover additional quantities of organic material, if desired. Residual water can be removed from the organic phase by any desired technique, such as stripping under vacuum, to recover the product.

In some modes of practice, the second reaction step may be carried out over a range of temperatures. In one such advantageous mode, for instance, the addition of the hydrocarbyl halide to the reaction vessel is initiated at a first relatively high temperature, and then the temperature of the vessel contents is lowered in one or more steps, or continuously during at least a portion of or throughout the remaining addition of the hydrocarbyl halide. Because the second reaction tends to be exothermic in many instances, the hydrocarbyl halide is introduced slowly enough, and the reactor is cooled, to facilitate the desired cooling profile. This mode of practice has advantages of both the high and low temperature reaction steps provided herein. First, because at least a portion of the second reaction occurs at relatively higher temperature(s), low color advantages of the higher temperature and/or pre-heating options (described further herein) are achieved at least to a large degree. Further, because at least a portion of the second reaction step occurs at relatively cooler temperature(s), the hydrocarbyl halide can be used at or close to the stoichiometric amount.

The principles of the present invention may involve forming a dimethyl ether from a monomethylether polyethylene glycol (mPEG). An mPEG as used in this reaction scheme is a linear polyether polymer incorporating two or more oxyethylene (EO) repeating units and may be represented by the formula $$CH_3O-(CH_2CH_2O)_n-H$$

wherein n is 2 to 20,000 and preferably is a number such that the PEG has a weight average molecular weight in the range of from about 150 to about 25,000, preferably from about 200 to about 15,000, more preferably from about 260 to about 1000. This can be converted to a dialkyl ether in the practice of the present invention by reaction with a hydrocarbyl halide. For purposes of illustration, the following reaction scheme uses methyl chloride and NaOH as the hydrocarbyl halide and base, respectively:

$$CH_3O-(CH_2CH_2O)_n-H+NaOH \rightarrow CH_3O-(CH_2CH_2O)_{n-1}CH_2CH_2O^-Na^++H_2O \qquad (1)$$

$$CH_3O-(CH_2CH_2O)_{n-1}CH_2CH_2O^-Na^+ + CH_3Cl \rightarrow CH_3O-(CH_2CH_2O)_n-CH_3+Na^+Cl^- \qquad (2)$$

Suitable mPEGs are often commercially available as a mixture containing a distribution of polymers with varying number of repeating units and a corresponding variation in molecular weight. In such mixtures, each alcohol would react with the base and the hydrocarbyl halide in the manner shown above to yield a corresponding mixture of the dimethyl diethers. Thus, the present invention can also be used to prepare any of the dialkyl ethers of the polyoxyalkylene glycols described in U.S. Pat. Nos. 2,649,166; 3,362,133; 3,591,641; 3,737,392; 3,824,766; 3,837,143; 4,044,100; 4,581,154; 4,741,745; 4,946,620; 4,995,888; 5,273,679; and 6,592,779; and EP 146886. Each of these patent documents is incorporated herein by reference in their respective entireties for all purposes.

Another class of monoalkylether polyoxyalkylene alcohol (mPOA) reactant suitable as alkoxide precursor materials that would be useful in the practice of the present invention are copolymers at least incorporating one or more oxyethylene and one or more oxyisopropylene (PO) repeating units according to the formula $$R^3O(CH(CH_3)CH_2O)_m-(CH_2CH_2O)_n-H$$

wherein $R^3$ is straight, branched, or cyclic alkyl, preferably alkyl of 1 to 12 carbon atoms, often 1 to 3 carbon atoms; m is 1 to 20,000; n is 1 to 20,000; and m+n preferably is a number such that the mPOA has a weight average molecular weight in the range of from about 150 to about 25,000, preferably from about 200 to about 3000, more preferably from about 260 to about 1,000. Desirably, the ratio of m to n may be in the range from about 1:4 to about 4:1, preferably about 1:1.5 to 1.5:1. In this formula, the other isomer of oxyisopropylene may be present.

The present invention can also be used to convert alcohols such as $CH_3O(CH_2)_zOH$ to $CH_3O(CH_2)_zOCH_3$, wherein z is 1 to 1000, desirably 1 to 6. Dimethoxyethane is one example of a commercially important diether according to this formula. This formula shows methyl as the terminal alkyl groups. Other alkyl groups may be present in alternative embodiments.

Some alcohol reactants that serve as alkoxide precursors include impurities that can lead to undesirable color formation in the final product. For instance, monomethyl-capped polyethylene glycol mixtures often include such impurities. Color formation can cause the resultant ether product to fail to meet applicable product specifications. For instance, a typical polyalkylene glycol dialkyl ether solvent might be subject to a color specification that requires a Gardner number of less than 3. The present invention provides multiple strategies that limit these impurities and thereby reduce the occurrence of undue coloration. These strategies can be used singly or in combination. Mono-methyl-capped polyethylene glycol mixtures can be reliably converted to dimethyl ethers having Gardner numbers of about one or less using principles of the present invention.

According to one strategy applicable to those modes of practice in which the second reaction step occurs at a temperature above about 90° C., or even above about 100° C., or even above about 110° C., it is desirable to preheat the contents of the reaction vessel resulting from step one before adding the hydrocarbyl halide to the vessel. The vessel contents may be heated up to and optionally may be held at a desired temperature for a period of time before adding the hydrocarbyl halide. Such period of time may range from 10 seconds to 8 hours, desirably 1 minute to 4 hours, more desirably 10 minutes to 2 hours. After pre-heating in this way, the hydrocarbyl halide can then be introduced to the vessel. It has been found that delaying addition of the hydrocarbyl halide until after pre-heating helps reduce coloration issues. In contrast, it has been found that the product is much more prone to coloration if the hydrocarbyl halide is present during the entire temperature ramp.

According to a second strategy, the reaction between alkoxide and hydrocarbyl halide is carried out at a temperature above 110° C. This strategy may be carried out in combination with the pre-heating strategy. Without wishing to be bound by theory, it is believed that the impurities that lead to color issues are consumed at such relative high temperatures.

As a third strategy, an impurity scavenger (also referred to as a decoloring agent) that consumes these impurities can be added to the vessel preferably before the base is added. Optionally, the resultant combination can be mixed for a period of time prior to adding the hydrocarbyl halide. An exemplary impurity scavenger is $NaBH_4$. It is believed that the agents responsible for undesirable coloring are aldehydic in nature and that the color forms at least partially upon addition of the base. This theory is borne out by the fact that $NaBH_4$ helps reduce coloring problems and is a reducing agent. Other reducing agents that could be suitable include sodium metabisulfite, charcoal, and other color reducing agents known to one skilled in the art, combinations of these, and the like. Such an impurity scavenger is often desirably used when the reaction is carried out at lower temperatures, e.g., less than about 110° C., even less than 75° C., or even less than about 50° C. Using from about 2 ppm to 500 ppm, desirably 10 ppm to 100 ppm of such a material based upon the weight of the alcohol reactant would be suitable in many embodiments.

Formate by-products can also be an issue in ether reactions. For instance, formate by-products can be a concern when forming dimethyl ethers from monomethyl polyethylene glycol precursors. The formate impurities are undesirable, because their formation indicates a loss of yield, they can be corrosive, and can have a negative impact on the end-use application. The present invention offers multiple strategies to minimize formate by-products. Firstly, the both reaction steps are carried out in an atmosphere in which the oxygen content is reduced with respect to the ambient. More preferably, the reaction medium is isolated from oxygen as much as is practical. To this end, the reaction vessel and conduits conveying materials to the vessel are purged and filled with nitrogen, argon, carbon dioxide, mixtures of these, and the like. A blanket of one or more of these gases is maintained in the headspace, if any, above the reaction medium. A positive pressure is maintained in the reaction vessel to help establish a pressure bias to keep the ambient atmosphere out. Agitation is carried out in a manner to ensure that air from the ambient is not entrained in any of the reactants before or during the reaction. Also, the reactants can be degassed prior to being introduced into the reaction vessel.

The present invention will now be described with reference to the following representative examples.

Example 1

A total of 455 weight parts of a methoxypolyethylene glycol (MW=260 g/mole) were charged to a 316 stainless steel jacketed baffled reactor equipped with an agitator that has 2 sets of 3 pitched blades. The reactor was purged and evacuated with nitrogen, and was opened while under a continuous nitrogen sparge to charge 100 weight parts of sodium hydroxide (1.43 equivalents) through a nozzle from the top of the reactor while maintaining the temperature below 40° C. by cooling with water. After the addition of all the sodium hydroxide, the reactor was pressured with nitrogen to 15-20 psig and evacuated to 1-2 psig three times, leaving 1-2 psig on the reactor. The reactor was heated to 120° C. and the addition of methyl chloride was begun. A total of 98 weight parts (1.11 equivalents) of methyl chloride were fed from a cylinder through a dip tube which enters from the top of the reactor and goes to the bottom at a rate to maintain a pressure of 12-16 psig and a temperature of 110-120° C. with cooling, and towards the end of the reaction by heating. A total of 278 weight parts of water were added and the layers were separated at 89° C. Residual water was stripped from the product under vacuum (5-10 mm) while maintaining the temperature below 96° C. A total of 420 weight parts (87.6% recovery) of product were obtained.

Example 2

Procedure was the same in Example 1 except the reactor was held at 120° C. for one hour before the addition of methyl chloride. The product was removed from the salt by centrifugation. The finished product had good color and was low in formates.

Example 3

2863 g (1.0 mole equivalents) of a polyalkylene glycol monomethyl ether (hereafter referred to as glycol ether) having an average molecular weight of 260 were charged to a pressure reactor fitted with a solids dispersion agitator. 0.24 g of 12% sodium borohydride solution was added such that the level of sodium borohydride was 10 ppm based on the charge of glycol ether. The batch was then mixed for 30 minutes to ensure dispersion and effective use of the sodium borohydride. 613 g (1.4 mole equivalents) of solid sodium hydroxide (micropearl) were charged whilst maintaining agitation. The batch was then mixed for 30 minutes before proceeding to the next stage. 556 g (1.0 mole equivalents) of methyl chloride were fed to the reactor over a period of 6 hours while cooling was applied to maintain the batch at a temperature of 40° C.-45° C. The batch was held at 40-45° C. for a further 4 hours after which the reactor was vented. The batch was then washed with water to remove the sodium chloride and excess sodium hydroxide. The washed product was dried by heating under vacuum to distil out the water. The dried product was filtered to remove the small amount of sodium chloride that remained. The final product represented a conversion of 99.5% of the glycol ether to the glycol diether. The glycol diether recovered from the process represented a yield of 98% based on the charge of glycol ether. The above process illustrates that the reaction was carried out at high conversion and high yield at low temperature in a short time using only the stoichiometric amount of alkyl halide.

Example 4

664 grams of a polyalkylene glycol monomethyl ether having an average molecular weight of 260 was charged to a pressure reactor along with 135 grams (1.28 molar equivalent) of solid sodium hydroxide. The reactor was heated to 120° C. over 1 hour and then held at temperature for an additional 1 hour. 135 grams (1.05 molar equivalent) of methyl chloride was metered into the reactor over a span of three hours. Concurrent to the methyl chloride feed, the vessel temperature was reduced to 80° C. in a linear fashion. The reactor was held at 80° C. overnight to allow all the methyl chloride to react. The color of the resultant product was less colored than the starting material by one Gardner unit. This color change was equivalent to a similar run done at a constant temperature of 120° C. The final product represented a conversion of 97.6% of the glycol ether to the glycol diether, which was 1.6% higher than an equivalent test run at 120° C. showing the overall better efficiency of the methyl chloride at lower temperatures.

What is claimed is:

1. A method of making an ether, comprising the steps of:
   a) reacting an alcohol with at least a 20 molar percent stoichiometric excess of a hygroscopic base to form an intermediate product mixture comprising an alkoxide anion and excess base, said reaction occurring under conditions such that the base functions as a scavenger to scavenge by-product water to help drive the reaction toward completion;
   b) preheating the intermediate product mixture to a temperature greater than about 110° C.; and
   c) in the presence of the excess base, adding a stoichiometric excess of a hydrocarbyl halide to the pre-heated intermediate product mixture and reacting the alkoxide anion with the hydrocarbyl halide at a temperature greater than about 110° C. to form a product mixture comprising an ether.

2. The method of claim 1, wherein the alcohol comprises a terminal ether moiety and step (c) comprises forming an ether comprising said terminal ether moiety and an additional terminal ether moiety.

3. The method of claim 1, wherein the alcohol comprises a monoalkyl ether (poly)oxyalkylene alcohol having from 2 to 10,000 oxyalkylene units.

4. The method of claim 1, further comprising the steps of adding a sufficient amount of water to the product mixture to form an aqueous phase and an organic phase; separating the phases; and recovering the ether from the organic phase.

5. The method of claim 1, wherein a first portion of step (c) comprises reacting the alkoxide anion with the hydrocarbyl halide at a temperature greater than about 110° C. and a second portion of step (c) occurring after the first portion is carried out at a temperature below about 75° C. and in the presence of a decoloring agent.

6. The method of claim 3, wherein the steps step (a) and step (c) occur under a non-ambient atmosphere and a positive pressure relative to the ambient.

7. The method of claim 1, wherein at least a portion of the excess base is in the form of suspended particles during at least a portion of the reaction between the hydrocarbyl halide and the alkoxide anion.

8. The method of claim 7, wherein a first portion of step (c) comprises reacting the alkoxide anion with the hydrocarbyl halide at a temperature greater than about 110° C. and a portion of step (c) occurring after the first portion occurs at a temperature below about 75° C.

9. A method of making an ether, comprising the steps of:
   a) reacting an alcohol with at least a 20 molar percent stoichiometric excess of a hygroscopic base to form an intermediate product mixture comprising an alkoxide anion, remaining alcohol, excess base, said reacting occurring at a first temperature, said reaction occurring under conditions such that the base functions as a scavenger to scavenge by-product water to help drive the reaction to completion;
   b) heating the intermediate product mixture to a second temperature greater than the first temperature and greater than about 110° C.;
   c) optionally holding intermediate product mixture at a third temperature greater than the first temperature and greater than about 110° C.; and
   d) in the presence of the excess base and the remaining alcohol, adding a stoichiometric excess of a hydrocarbyl halide to the intermediate product mixture and reacting the alkoxide anion with the hydrocarbyl halide at a temperature greater than about 110° C. to form a product mixture comprising an ether.

10. The method of claim 9, wherein at least two of the second, third and fourth temperatures are substantially the same.

11. The method of claim 1, wherein step (d) is carried out in the presence of the hygroscopic base in finely divided solid form.

12. The method of claim 1, wherein the alcohol has the formula ROH wherein R is selected from a straight, linear or branched monovalent moiety other than H.

13. The method of claim 12, wherein the ether is a diether.

* * * * *